United States Patent [19]

Jones

[11] 4,308,974
[45] Jan. 5, 1982

[54] TAMPON DISPENER

[76] Inventor: Linda M. Jones, 1508 Stanford Way, Sparks, Nev. 89431

[21] Appl. No.: 125,910

[22] Filed: Feb. 29, 1980

[51] Int. Cl.³ .............................................. B65H 3/00
[52] U.S. Cl. .................................. 221/196; 221/203; 221/266
[58] Field of Search .............. 221/266, 202, 203, 204, 221/205, 200, 196; 222/228, 230

[56] References Cited

U.S. PATENT DOCUMENTS

| | | | |
|---|---|---|---|
| 995,157 | 6/1911 | Korman | 221/266 |
| 1,146,447 | 7/1915 | Prommel | 221/266 |
| 1,237,919 | 8/1917 | Linkiewicz | 221/266 |
| 1,518,933 | 12/1924 | Kantor | 221/266 X |
| 1,773,329 | 8/1930 | Upham | 221/266 |
| 2,075,988 | 4/1937 | Johnson | 221/204 |
| 3,248,008 | 4/1966 | Meirjohan | 221/205 |

*Primary Examiner*—Allen N. Knowles
*Attorney, Agent, or Firm*—Herbert C. Schulze

[57] ABSTRACT

This invention is a device for the discreet storage and dispensing of tampons. The device is characterized by including a storage container having a dispensing apparatus which will dispense one tampon at a time without display except when actually dispensed and wherein it is dispensed by means of an elongated member having a suitable pocket therein for said purpose. It is further characterized by being suitable to accommodate different sizes of commonly used tampons.

1 Claim, 16 Drawing Figures

U.S. Patent  Jan. 5, 1982  Sheet 1 of 3  4,308,974
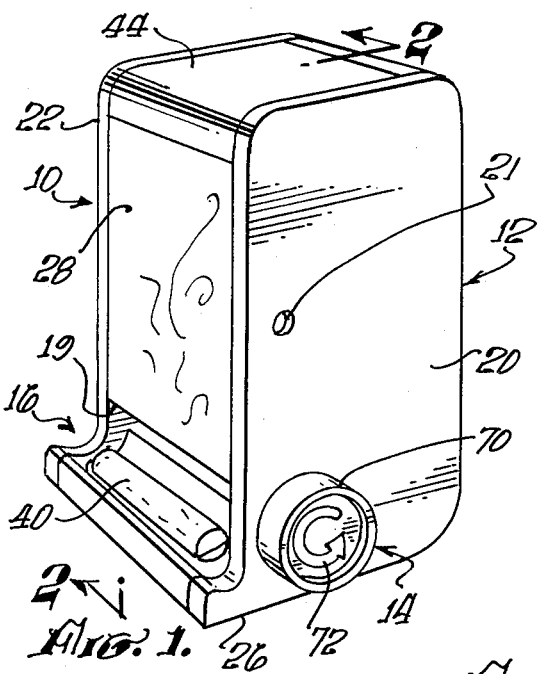
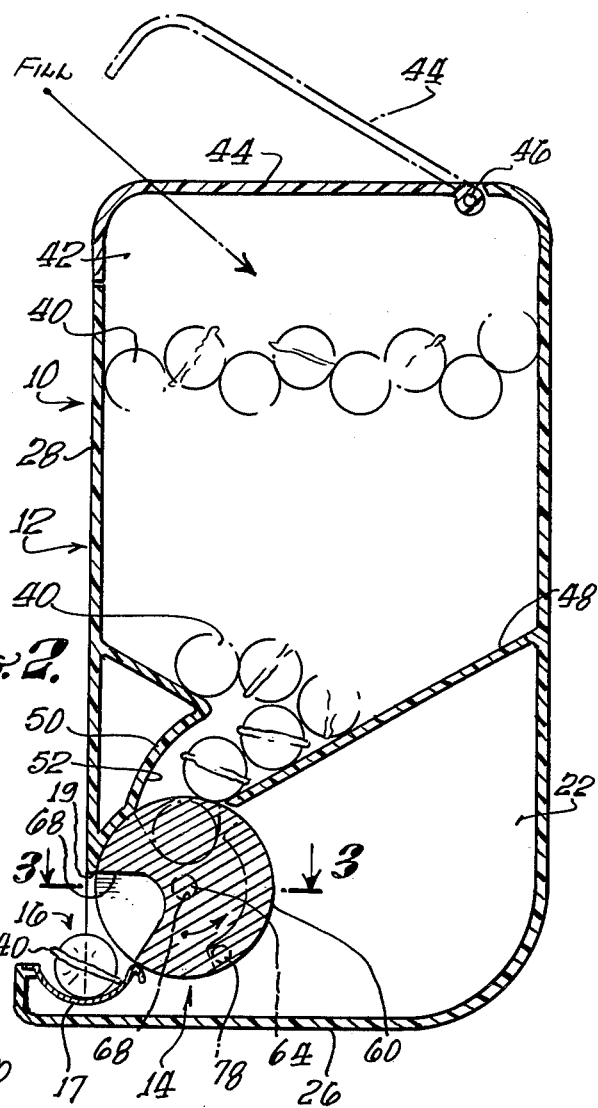
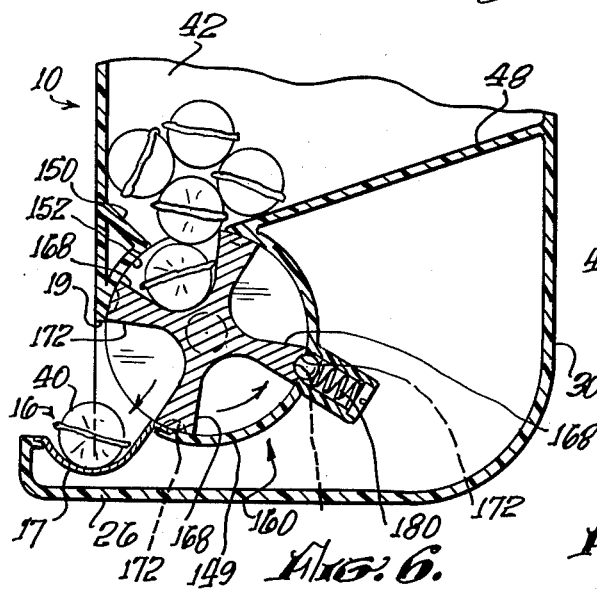
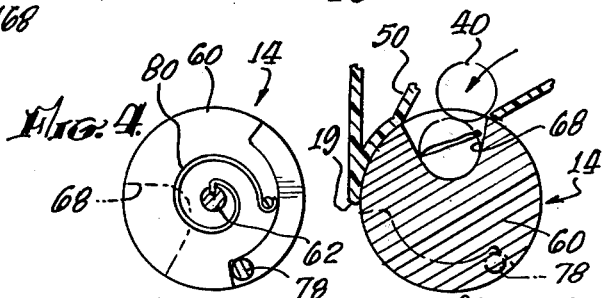
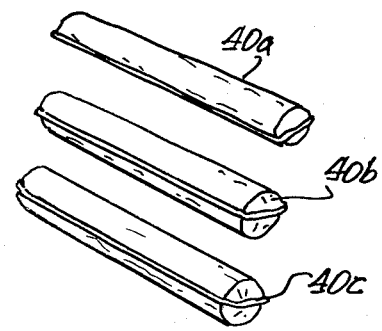
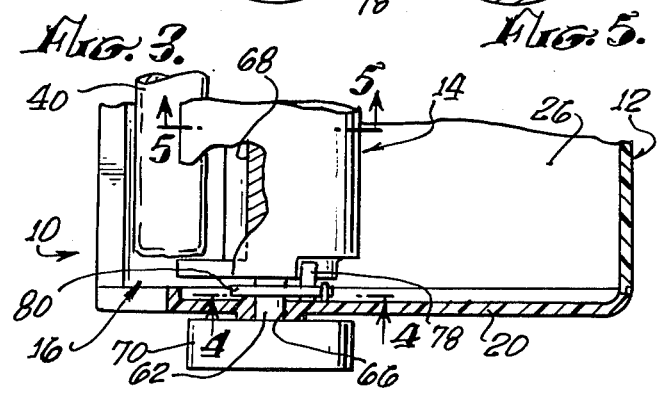

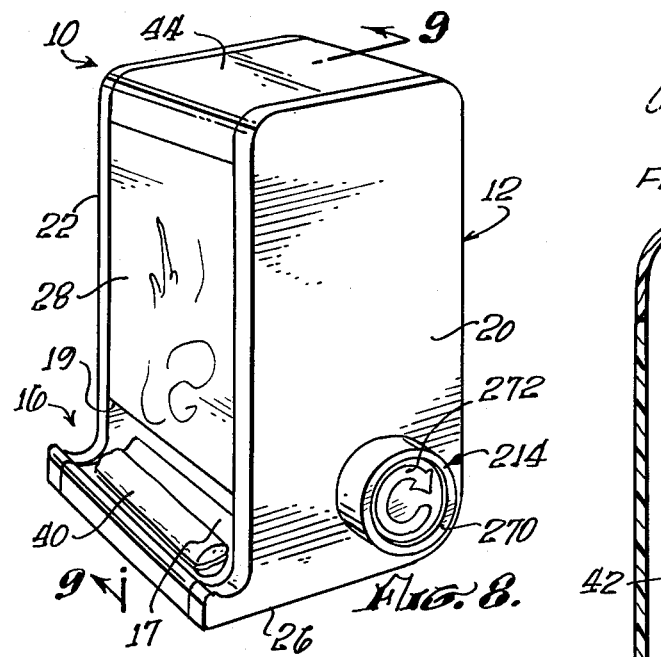
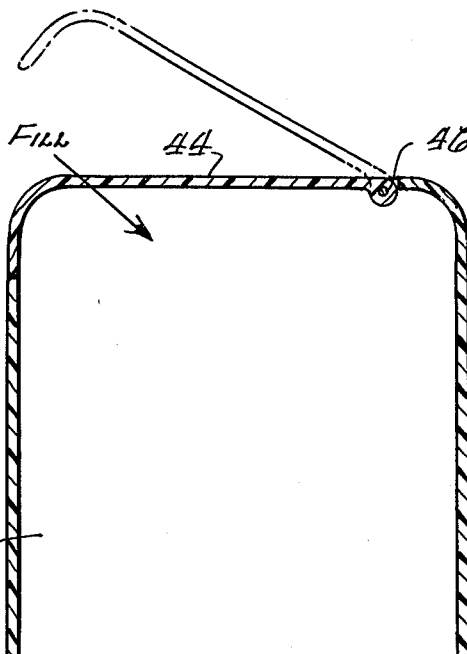
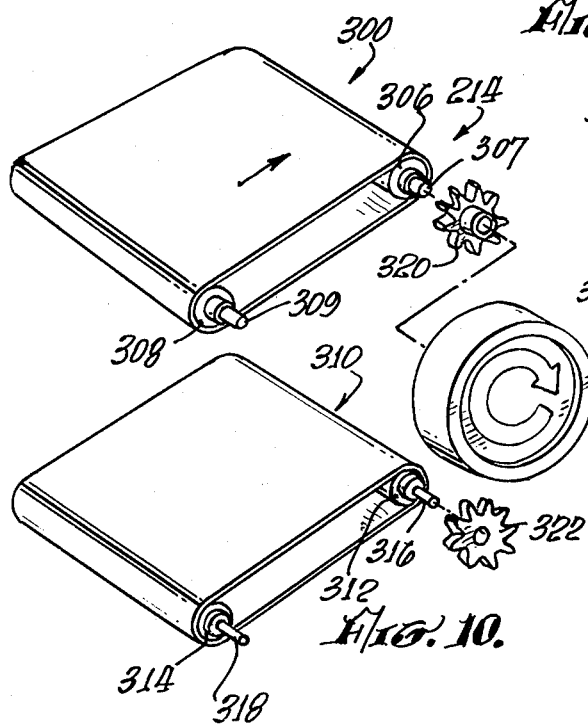
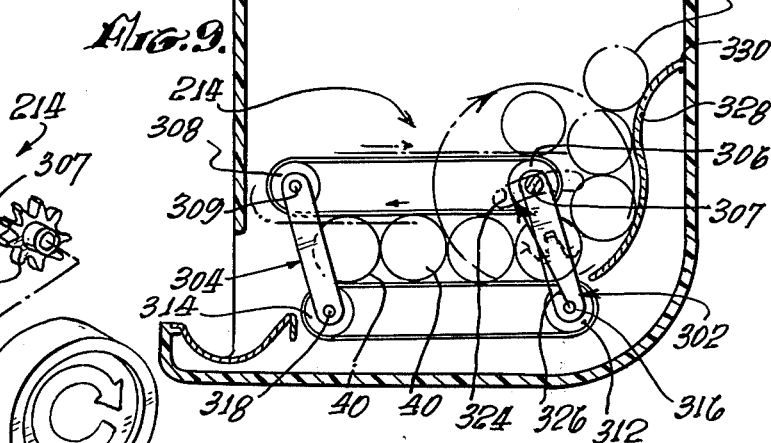
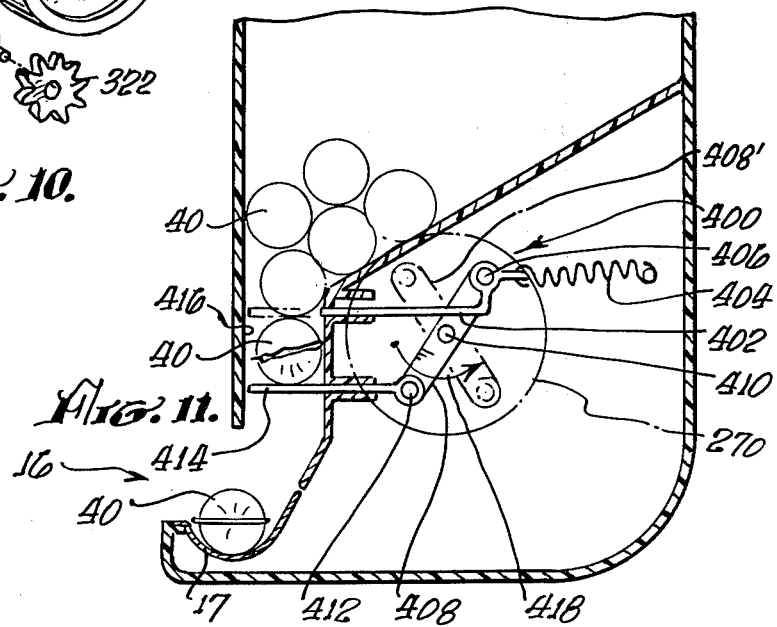

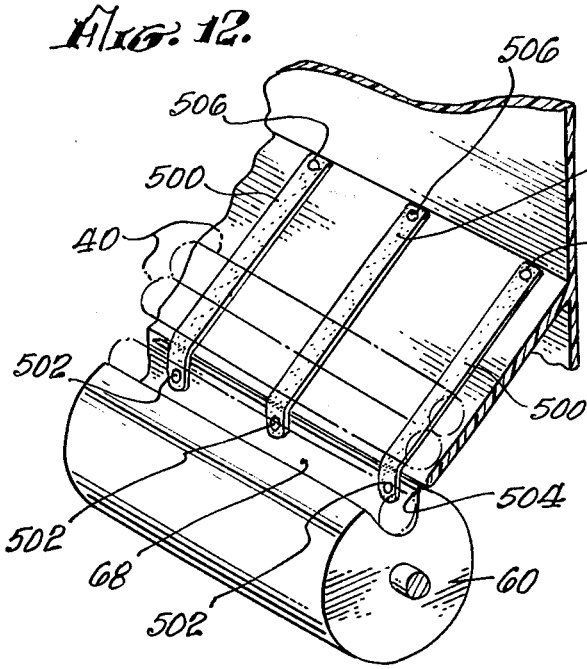
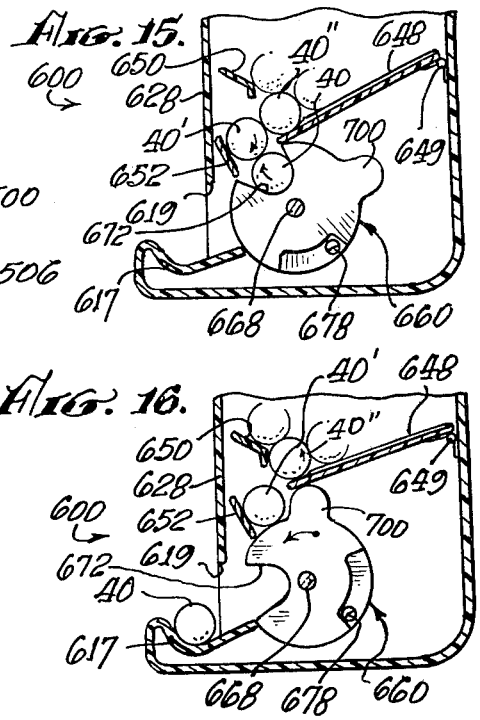
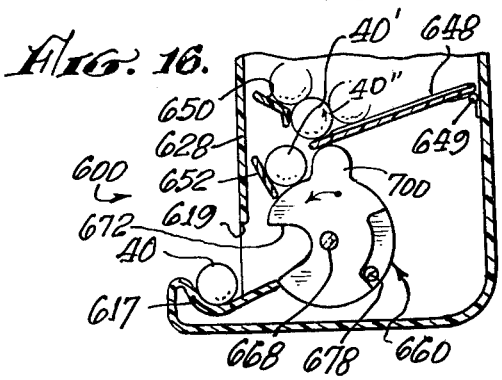
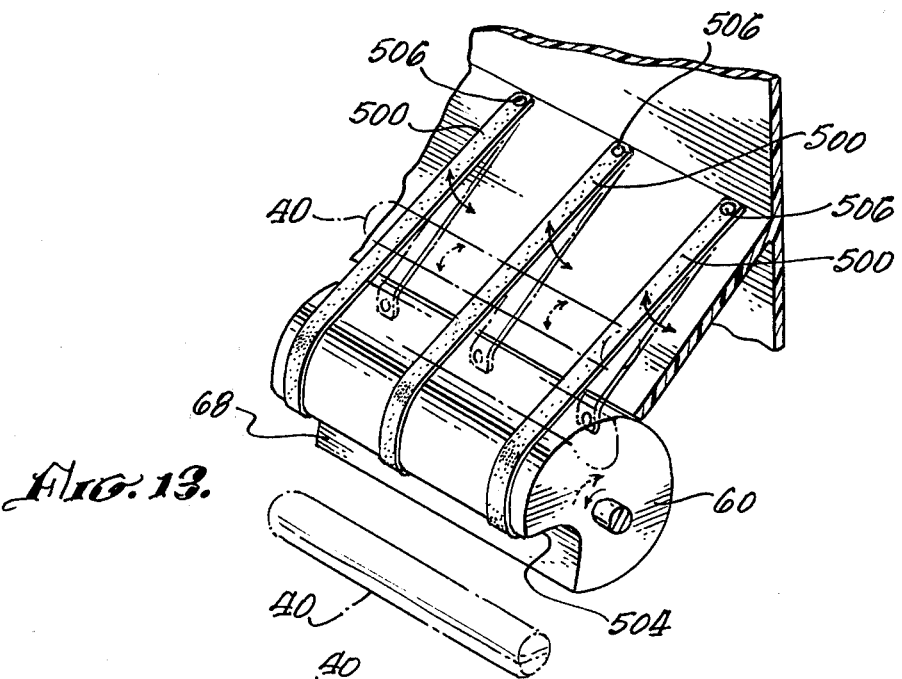
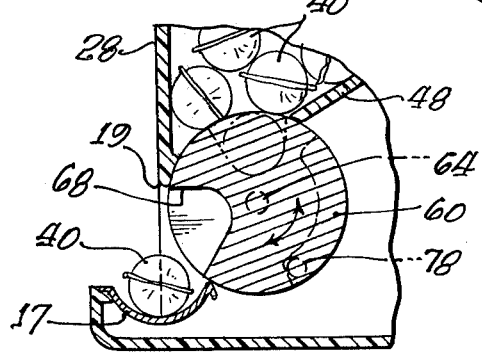

TAMPON DISPENER

CROSS REFERENCE TO RELATED PATENTS

There are no patent applications previously filed by me relating to this invention.

BACKGROUND OF THE INVENTION

1. Field of the Invention

This invention is in the general field of dispensers and is more particularly directed to a storage container and dispenser for tampons and is even more particularly related to such a storage and dispensing device wherein a single tampon is dispensed when desired, but wherein no others are subject to view except when actually dispensed.

2. Description of the Prior Art

It is known that there are many dispensers for various types of articles on the market. There are even commercial dispensers for tampons wherein a sum of money is placed into a machine in return for a tampon. These commercial devices for tampons, particularly, normally provide for tampons stacked in rows and dispensed by a somewhat complex mechanism.

Other types of dispensers run a very wide range such as cigarette dispensers, chewing gum dispensers, candy dispensers, toothpick dispensers, and the like. Of all of these dispensers known to me perhaps the closest is a toothpick dispenser. However, a toothpick dispenser is not at all anticipatory of the present invention since there are unique problems related to the dispensing of tampons in a discreet manner. First, the tampons must be stored in an inconspicuous manner and secondly, the apparatus must be suitable to accommodate a range of different sizes which are somewhat difficult of dispensing because they are wrapped and not in a perfectly configured package. Thus the present invention is believed to be without any truly comparative prior art.

THE SUMMARY OF THE INVENTION

Tampons are used by many women for their personal periodic feminine requirements. In general, there are three different sizes which are used according to the individual requirements at the time.

It is desirable to most persons to maintain their supply of tampons in an inconspicuous manner and at the same time, however to be convenient for individual dispensing.

This present a problem which is not quite as simple as might be thought. The ability to accommodate different sizes with an economical and nor unduly bulky container is necessary. Additionally, ease of dispensing of one item is quite important, but at the same time it is essential to many persons that a next available tampon not be available to sight.

After studying this problem at some length, and after considering many complex dispensing mechanisms and the like, I have now developed a discreet, attractive, uncomplicated, and economical apparatus for this purpose.

In solving the problem, I have produced a container having a suitable opening wherein a complete package of tampons may be stored. Within the container there are provided guiding shelves inclined in such manner that the tampons will move downward to a desired position where I have placed a long member containing a dispensing pocket which is activated by a handle exterior of the container. When the handle is activated, one tampon is dispensed through the pocket. As the one tampon is picked up and dispensed by activation of the dispensing pocket, a protective member follows the pocket in such manner that a second tampon cannot move downward from its support shelf within the container.

After the one tampon is dispensed, the dispensing pocket returns to its normal position either by automatic spring return or the like, or my manual return. It is then available for the next dispensing.

It is an object of this invention to provide a tampon dispenser which will dispense various sizes of tampons.

Another object of this invention is to provide a tampon dispenser which holds a supply of tampons out of view and only dispenses one tampon at a time when desired.

Another object of this invention is to provide such a tampon dispenser as is herein described which prevents dispensing and view of tampons until one is actually desired.

The foregoing and other objects and advantages of this invention will become apparent to those skilled in the art upon reading the description of a preferred embodiment which follows, in conjunction with a review of the appended drawings.

BRIEF DESCRIPTION OF THE DRAWINGS

FIG. 1 is a perspective view of a preferred embodiment of the invention as viewed from the top, front and right side;

FIG. 2 is an enlarged sectional view taken on line 2—2 of FIG. 1;

FIG. 3 is a fragmentary sectional view with certain parts in elevation, as viewed on line 3—3 of FIG. 2;

FIG. 4 is a sectional view as viewed on line 4—4 of FIG. 3;

FIG. 5 is a sectional view taken on line 5—5 of FIG. 3;

FIG. 6 is a sectional view similar to FIG. 2 but showing a modified form of the invention;

FIG. 7 is a perspective view showing different sizes of the tampon that will be dispensed by this invention;

FIG. 8 is a perspective view of a second modification of the invention;

FIG. 9 is an enlarged sectional view taken on line 9—9 of FIG. 8;

FIG. 10 is an exploded perspective showing various elements used in the construction of FIGS. 8 and 9;

FIG. 11 is still a further modification of my dispensing device;

FIGS. 12 and 13 are schematic perspective indications of a method of agitating the tampons during the dispensing procedure;

FIG. 14 is an alternate embodiment of the interior of the dispenser; and

FIGS. 15 and 16 show a further dispenser embodiment.

DESCRIPTION OF A PREFERRED EMBODIMENT

FIGS. 1 through 4 illustrate a preferred embodiment of an absorbent tampon dispensing device generally indicated by the reference numeral 10. The dispenser comprises a housing 12, a metering and ejecting unit 14 and a tray portion 16.

As viewed in the FIG. 1 perspective and the cross-section of FIG. 2, side walls 20 and 22, top and bottom portions 24 and 26, front and rear walls 28 and 30, form a container for storing and dispensing commonly marketed cylindrically shaped elongated absorbent tampons. These tampons as indicated in FIG. 7 may be of several different diameters ranging from small to large, but to those familiar in the art are commonly sold in sizes called "regular" and "super". In FIG. 7 I have indicated these tampons as 40a, 40b and 40c.

Obviously, it has been a problem to dispense such items because of the variance in diameter. I have designed a means of accommodating any of these sizes into one unit which can positively and freely dispense one unit at a time for easy removal.

As shown in the section of FIG. 2, the tampons 40 are placed into storage area 42 by lifting a lid 44 which is hinged at 46. At the bottom of the space 42, I have provided a downwardly tapering bottom wall 48 in spaced relationship with a wall portion 50 to create a channel 52 into which no more than one tampon 40 can fall by gravity at one time.

The metering device 14, as seen in FIGS. 2 and 3 comprises a cylindrical body portion 60 having stub shafts 62 and 64 rotatably mounted in openings 66 and 68 of side walls 20 and 22, is provided with a slot or channel 68 of a configuration that will accommodate all of the various sizes, referred to previously, of the tampon 40. The shaft portion 62 extends beyond the housing of sufficient distance to have a knob 70 to be fastened thereto.

When it is desired to dispense a single tampon, an operator only needs to rotate knob 70 in the direction of the arrow 72 indiciated in FIG. 1, thereby moving the cylinder 60 from the FIG. 5 position to the FIG. 2 position. A semicylindrical slot 70 having end walls 72 and 74, and a side wall 76 provides a limiting channel for a pin 78 fixedly mounted to the side wall 20, provides a limiting means to properly orient the filling and ejecting positions of slot 68.

Familiar to everyone in such arts, a spiral spring 80 can be provided to return the cylinder 60 to its initial loading position after knob 70 had been rotated to the dispensing position and then released.

In FIG. 6 I have provided a metering cylinder 160 which may have a plurality of tampon accepting compartments 168, in order to allow a continuous single direction rotation of knob 70 and not needing a return spring. A ball detent 178 is urged by a spring 180 into recesses 172 upon every rotation of knob 70 during one dispensement of a tampon 40.

Bottom wall construction 48 and spacer wall 150 provide a channel 152 allowing a single tampon at a time to be dropped into the metering compartments. The empty compartments that are not in use are enclosed by a circular wall 149.

When the individual tampon has been released from the metering unit 14, it is dropped onto a tray portion 16 having a semi-circular plate 17 to cradle the tampon until the operator reaches in through the opening 19 of walls 28. It is not inconceivable that with many members of a family using different sizes of tampons that the compartment 42 may have a variety of trade names and different diameter types which can be dispensed one at a time onto the tray portion 16. If the tampon is of the improper size, it can be replaced by opening lid 44 and the operation continued until the desired article has been dispensed.

In FIGS. 8 through 10 I have provided a second modification of a metering mechanism 214. In this design, by simply rotating knob 270 in the direction of arrow 272 one can intermittently have one tampon 40 dropped into the tray 16. As seen in the FIG. 10 perspective, conveyer type belt assemblies 300 and 310 are rotatably mounted to pairs of arms 302 and 304 as can be seen in FIG. 9. Rollers 306 and 308 of the upper movable assembly 300 are provided with extending stub shafts 307 and 309, respectively. The fixed conveyer assembly 310 with its cylindrical members 312 and 314 is also provided with stub shaft extensions 316 and 318. These latter stub shafts are also rotatably mounted at the lower end of pairs of arms 302 and 304. When an operator rotates knob 270 in the direction indicated by the arrow 272, the drum 306 pulls the conveyor 300 into a direction so as to advance a series of tampons 40 toward the opening 19 of the housing 12 of the container. The lower conveyor assembly 310 also moves about cylinder 312 and aids in moving the tampons along. This is accomplished by affixing gears 320 and 322 to stub shafts 307 and 316.

When a different size tampon is being moved through the metering and advancing unit 214, the upper movable roller assembly 300, automatically is raised to another position indicated by phantom lines 300' of FIG. 9. Stub shaft 307 extends out through an arcuate slot 324 in side wall 20 of housing 12 allowing a movement along a radius 326 struck about a point along the axis of shaft 316. A spring-like backing plate 328 fixed at 330 to wall 30 can compensate for allowing various diameters to move down into the area between belt assemblies 300 and 310.

Additionally, I have indicated a third modification of a metering device indicated by the reference numeral 400. In this form a spring loaded gate 402 held in an open condition by means of spring 404 is pivotally mounted at 406 to an arm 408. This arm is affixed to a shaft 410 which is actuated by a knob 270. At the opposite end of arm 408 is pivotally mounted at 412 a lower gate 414. As can be very easily understood, a tampon 40 which has been allowed to drop into a channel 416 by means of the withdrawl of gate 402, is now resting on lower gate 414 and is ready to be dispensed onto tray 16. When the operator rotates knob 270 in the direction of the arrow 418, it can be seen that the upper gate moves forward and cuts off the possibility of more than one tampon to enter the throat 416. At the same time that this motion is being accomplished lower gate withdraws to the phantom position 408' of the arm 408 allowing the tampon to fall.

As viewed in FIG. 1, I have provided an opening 21 in a location indicated on the drawings providing a view into the housing 12 in order to be able to observe if the tampon supply is being exhausted. Additionally, a conventional counter (not shown) may be added which would be actuated by knob 70.

FIGS. 12 and 13 show a special agitating means which can be utilized for purposes of preventing a number of tampons from "bridging" over the dispensing apparatus and thus cause a malfunction, or failure to dispense due to the inability to receive a tampon. Any type of agitation device could be ustilized to assist in this problem, but the present solution is unique and effective. It will be noted that a plurality of flexible bands 500 are mounted to the slot 68 of dispensing drum 60. These may be by means of rivets or the like, 502. The other end of the bands are mounted in a similar manner to the shelf 48 once again by rivets or the like 506.

It will be clear that as the dispensing member 60 is rotated, the elestic bands 500 will stretch and rise slightly from the shelf 48. Also, when the member 60 is returned to its normal position the elastic bands 500 will retract to their normal position. Thus, the supply of tampons will be agitated in both directions of movement of the dispensing apparatus. By means of this agitation any bridging effect is defeated and continued proper operation is assured.

FIG. 14 illustrates a different configuration on the interior of the apparatus as shown in FIG. 2 wherein the wall portion 50 has been removed thus eliminating the restricted channel opening 52. Under some circumstances this embodiment is preferred as there is also less tendency for the tampons to "bridge" when they are able to fill the entire area over the dispensing wheel. It will be noted that the shelf 48 remains as before and the wall 28 remains as before with dispensing apparatus filling the entire space between the end of the shelf 48 and the wall 28.

I have shown in FIGS. 15 and 16 another modification of the tampon dispenser 600. The metering cylinder 660 rotated by its shaft 668, has a projection 700 mounted thereto and as it is rotated in the direction of the arrow in FIG. 16, the projection lifts a moveable wall 648 hinged at 649 to the back wall of the container housing. This movement lifts and agitates a tampon 40'' while entrapping a tampon 40' into a waiting area formed by slot 672 and wall segment 652.

The tampon 40 which had been in slot 672 is thus dropped onto tray 617 through opening 619 in wall 628.

A movement limit pin 678 riding in an arcuate slot in cylinder 660 is provided.

As the cylinder 660 is returned to the position of FIG. 15 by spring action, the moveable wall 648 drops down by gravity allowing tampon 40'' to be next in line to be placed into the waiting compartment previously described.

While the embodiments of this invention shown and described are fully capable of achieving the objects and advantages desired, it is to be understood that such embodiments are for the purposes of illustration only and not for purposes of limitation.

I claim:

1. Tampon storage and dispensing means comprising in combination: a container suitable to hold a plurality of tampons; shelf means disposed within said container means and at a distance from the lower portion thereof suitable to guide tampons in a horizontal position; tampon holding means adjacent the lower edge of said container; tampon dispensing apparatus comprising an elongated cylindrical cylinder mounted intermediate said shelf means and said holding means, and comprising an elongated cylinder having located therein tampon holding means; means to rotate said elongated cylinder so as to move one tampon from the area of said shelf means to said holding means; and tampon agitating and moving means comprising at least one stretchable member associated with said shelf and intermediate said shelf and tampons in said container, which stretchable means is caused to be stretched upon rotation of said cylinder member.

* * * * *